(12) United States Patent
Rubin (10) Patent No.: US 11,488,011 B2
(45) Date of Patent: Nov. 1, 2022

(54) SCALABLE EXTENSIBLE NEURAL NETWORK SYSTEM AND METHODS

(71) Applicant: SPAWAR Systems Center Pacific, San Diego, CA (US)

(72) Inventor: Stuart H. Rubin, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 903 days.

(21) Appl. No.: 16/352,669

(22) Filed: Mar. 13, 2019

(65) Prior Publication Data
US 2020/0293879 A1   Sep. 17, 2020

(51) Int. Cl.
| | |
|---|---|
| G06N 3/08 | (2006.01) |
| G06F 1/16 | (2006.01) |
| A61B 5/00 | (2006.01) |
| A61B 5/242 | (2021.01) |

(52) U.S. Cl.
CPC .............. *G06N 3/08* (2013.01); *A61B 5/242* (2021.01); *A61B 5/6803* (2013.01); *A61B 5/7267* (2013.01); *G06F 1/163* (2013.01)

(58) Field of Classification Search
CPC ........ G06N 3/08; A61B 5/242; A61B 5/6803; A61B 5/7267; G06F 1/163
See application file for complete search history.

(56) References Cited

U.S. PATENT DOCUMENTS

| | | | |
|---|---|---|---|
| 7,047,226 B2 | 5/2006 | Rubin | |
| 7,840,506 B1 | 11/2010 | Rubin | |
| 8,073,804 B1 | 12/2011 | Rubin | |
| 8,117,147 B1 | 2/2012 | Rubin | |
| 8,155,949 B1 | 4/2012 | Rubin | |
| 8,250,022 B1 | 8/2012 | Rubin | |
| 8,280,831 B1 | 10/2012 | Rubin | |
| 8,315,958 B1 | 11/2012 | Rubin | |
| 9,299,025 B1 | 3/2016 | Rubin | |
| 9,396,441 B1 | 7/2016 | Rubin | |
| 2017/0281086 A1* | 10/2017 | Donaldson | ......... A61B 5/14542 |
| 2021/0248358 A1* | 8/2021 | Lee | ...................... G06K 9/6219 |

OTHER PUBLICATIONS

Chaitin, G.J., "Randomness and Mathematical Proof", Scientific American, vol. 232, #5, pp. 47-52, May 1975.
Eccles, J.C., "The Understanding of the Brain", McGraw-Hill, New York, NY, 1977 (2nd ed.), Chap 5.

(Continued)

*Primary Examiner* — Robert J Michaud
(74) *Attorney, Agent, or Firm* — Naval Information Warfare Center, Pacific; Kyle Eppele; Evan Hastings (57) ABSTRACT

A neural network system, involving a neural network, the neural network configured to: map sensor output to a Level 1 input; learn to fuse the time slices for one class, learning comprising taking and feeding a random assignment of inputs from each time slice into a threshold function for another two-dimensional array; learn to reject class bias for completing network training; use cycles for class recognition, and fuse segments for intelligent information dominance and a magnetic headwear apparatus operably coupled with the neural network.

20 Claims, 10 Drawing Sheets

(56) References Cited

OTHER PUBLICATIONS

Rubin et al., "KASER: Knowledge Amplification by Structured Expert Randomization", IEEE Transactions on Systems, Man, and Cybernetics—Part B: Cybernetics, vol. 34, No. 6, pp. 2317-2329, Dec. 2004.
Rubin, "On Randomization and Discovery", Information Sciences, vol. 177, No. 1, pp. 170-191, 2007.
Rubin et al., "On Heuristic Randomization as an Enabler of Domain Transference," 2015 IEEE International Conference on Information Reuse and Integration, Aug. 13-15, 2015, San Francisco, CA.

* cited by examiner

CYCLE 5   CYCLE 2

CYCLE 4   CYCLE 3

CYCLE 1

LET, CYCLE i DEFINE CLASS i.
OBSERVE THAT CLASSES 1, 3, AND 4 ARE ALL SIMILAR, WHILE CLASSES 2 AND 5 ARE DISTINCT. CLASSES 3 AND 4 ARE INSTANCES OF CLASS 1, WHICH IS MORE GENERAL. CLASSES 3 AND 4 ARE DISTINCT. CLASS 5 IS A STEADY STATE. THUS, THE CYCLES, OUTPUT BY LEVEL 3, ENABLE CLASS DISAMBIGUATION.

FIG. 5

TIME t-1

LEVEL 2 INPUT

TIME t
LEVEL 1 OUTPUT

SEGMENTS CAN VARY IN THE SIZE OF THEIR CHARACTERIZING ARRAYS. THEIR OUTPUTS CAN BE FUSED TO CREATE A NEURAL EXPERT SYSTEM FOR INFORMATION DOMINANCE. CYCLES ARE USED HERE, AS BEFORE, FOR CLASS DISAMBIGUATION.

SCALABLE EXTENSIBLE NEURAL NETWORK SYSTEM AND METHODS

FEDERALLY-SPONSORED RESEARCH AND DEVELOPMENT

The United States Government has ownership rights in the subject matter of this invention. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil. Reference Navy Case No. 103759.

BACKGROUND OF THE INVENTION

Technical Field

The present disclosure relates to neural network technology. Particularly, the present disclosure relates to neural network and magnetic imaging technologies.

Description of the Related Art

Figure 1:
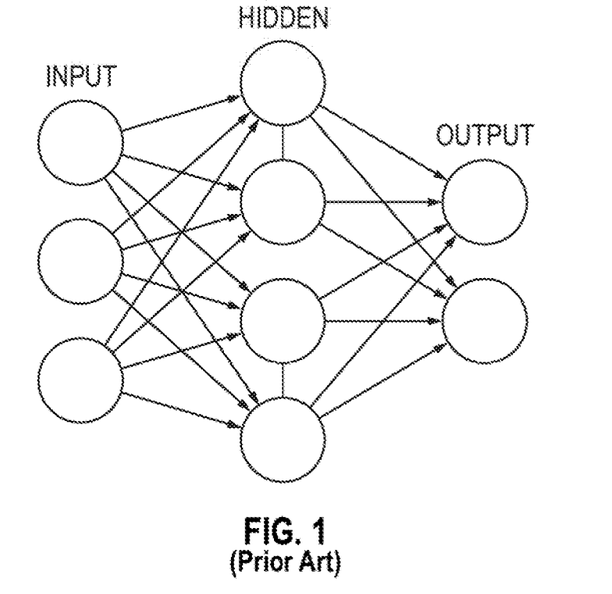
FIG. 1 is a diagram illustrating a conventional neural network, wherein each circular node represents an artificial neuron and an arrow represents a connection from the output of one neuron to the input of another, in accordance with the prior art.

In the related art, conventional artificial neural networks (ANN) represent a family of statistical learning models, derived from our biological neural networks. An ANN is represented by an interconnected group of nodes, which is similar in structure and function to the neurons in a brain. ANNs communicate among layers and attempt to minimize statistical error through training. The connections have numeric weights that can be adapted to minimize classification errors. ANNs are best suited to applications that are difficult, if not impossible, to realize using rule-based systems, including machine vision (visual recognition) and automated speech understanding (audio recognition). Referring to FIG. 1, each circular node represents an artificial neuron and, an arrow represents a connection from the output of one neuron to the input of another, in accordance with the related art.

Additionally, conventional neural networks attempt to randomize, together, many disjoint classes of knowledge. This type of randomization results in expending unnecessary exponential processing time. For example, the related art neural network devices, used in medical imaging, directly detect contemporaneous electrical signals from a scalp, wherein substantial noise interferes with detection. Classical related art neural networks, e.g., neural networks having at least one hidden layer, such a backprop, are NP-hard in their learning and are, thus, impractical.

Thus, a need exists in the related art for improving neural network learning, decreasing processing time, and decreasing signal interference.

SUMMARY OF THE INVENTION

The present disclosure addresses many of the challenges in the related art and generally involves a neural network system, comprising: a neural network, the neural network configured to: map sensor output to a Level 1 input; learn to fuse time slices for one class, learning comprising taking and feeding a random assignment of inputs from each time slice into a threshold function for another two-dimensional array; learn to reject class bias for completing network training; use cycles for class recognition; and fuse segments for intelligent information dominance; and a magnetic headwear apparatus operably coupled with the neural network.

BRIEF DESCRIPTION OF THE DRAWINGS

The above, and other, aspects and features of several embodiments of the present disclosure will be more apparent from the following Detailed Description of the Invention as presented in conjunction with the following several figures of the Drawings.

Corresponding reference numerals or characters indicate corresponding components throughout the several figures of the Drawings. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but wellunderstood, elements that are useful or necessary in commercially feasible embodiments are often not depicted in order to facilitate a less obstructed view of these various embodiments of the present disclosure.

DETAILED DESCRIPTION OF THE INVENTION

In order to address many of the related art challenges, the present disclosure generally involves a scalable extensible neural network system which enhances deep-learning and supports magnetic detection, such as superconducting magnetic brain signal detection. The neural network system of the present disclosure trades linear increases in required space for exponentially less required processing time. The neural network system of the present disclosure enables analysis of complex signals, whereby many signals are mappable to one set of semantics, tractable learning in space and time, analogical reasoning, utilization of massively parallel/distributed processors in an energy-conservative manner. The neural network of the present disclosure enables interpretation and magnetic signals from the brain as well as interpretation of other signals in the area of signal processing.

The neural network system and methods of the present disclosure further address the interrelated problems of sensing magnetic signals and interpreting magnetic signals, such as those magnetic signals relating to brain activity. The neural network system and methods of the present disclosure provide solutions to these interrelated problems via devices implementable in portable lightweight diagnostic apparatuses for field use in the diagnosis of head trauma. The neural network system and methods of the present disclosure also extend the envelope in "command-and-control" (C2) technology, such as in providing at least partial "thought-control" of military systems. Potentially thousands of variants exist within a class; and hundreds of classes are to be mapped to their semantics. The semantics associated with these classes are useful for the diagnosis of brain dysfunction as well as in the sensing of C2 thoughts for partial mind-control of military hardware. For example, C2 technology encompasses a set of organizational attributes, technical attributes, and processes, employing human resources, physical resources, and information resources for solving problems, and accomplishing missions, e.g., military missions.

Unlike the related art devices which directly detect contemporaneous electrical signals from a scalp, the neural network system and methods of the present disclosure encompass a plurality of superconducting quantum interference devices (SQUIDs) for facilitating detection of magnetic signals emanating from a brain, such as an array of SQUIDs, configured to detect very small magnetic fields produced by the brain, thereby greatly minimizing noise which otherwise interferes with detection. SQUIDs are sufficiently sensitive for measuring magnetic fields as low as approximately 5 aT ($5 \times 10^{-18}$ T) ("T" denoting Tesla units, and "aT" denoting attotesla units); and the noise levels are as low as approximately 3 $fT \cdot Hz^{-1/2}$. For example, a typical refrigerator magnet produces approximately 0.01 tesla ($10^{-2}$ T) while some animal processes produce very small magnetic fields in a range of approximately $10^{-9}$ T to approximately $10^{-6}$ T.

In an embodiment of the present disclosure, the neural network system encompasses a neural network and a magnetic headwear apparatus, the magnetic headwear apparatus comprising a "hat" or a headwear portion and an array of SQUIDs disposed in relation to the headwear portion and configured to dispose the array of SQUIDs in close proximity to a scalp, the array of SQUIDS configured to detect a magnetic signal in a range of approximately $10^{-9}$ T to approximately $10^{-6}$ T. The magnetic headwear apparatus further comprises a cryogenic feature for facilitating cooling the array of SQUIDs. The array of SQUIDs detects magnetic signals emanating from the brain through the scalp and delivers the detected magnetic signals to the neural network. The neural network is linear in its scalability; and the neural network is configured to learn fusing a plurality of spatial-temporal signatures within an allowed margin to account for variation. This margin allows for the recognition of analogical signatures in space and time. This capability, e.g., learning to fuse a plurality of spatial-temporal signatures within an allowed margin to account for variation, is implemented in embodiments of the present disclosure for at least that mapping sensed magnetic fields to corresponding semantics is generally a "many to one" operation.

Moreover, the neural network of the neural network system is indefinitely scalable in its number of fundamental memories and can run exponentially faster than related art benchmark neural networks, such as "backprop" using linearly more space in the number of fundamental memories. The neural network is operable by way of a set of executable instructions, e.g., comprising a neural algorithm, and is, thus, configured to run across a massive number of parallel processors, e.g., in a range of approximately 100 parallel processors to approximately 10,000 or more parallel processors, for effecting linear self-learning and recall and for conserving energy during self-training. Again, unlike the related art backprop algorithm, the neural network of the present disclosure is segmentable for hierarchical performance in a deep-learning system. The neural network is suitable for any implementation where training time, minimal space, similarity matching, and scalability are of paramount importance.

In embodiments of the present disclosure, an array entry is used to characterize a magnetic field response emanating from an array of points on the surface of the skull in real time. These responses are grouped into classes based on their known semantics. These responses can be used to diagnose brain health as well as identify a particular affliction. These responses can also be used as an interpreter for thought-based C2 operations, e.g., for the control of prosthetic limbs.

In embodiments of the present disclosure, these responses may comprise dynamic characterizing output (not static output), wherein the dynamic characterizing output is a function of temporal changes, whereby context for analysis is providable. These responses, corresponding to temporal changes, are captured by the neural network system through the use of feedback. The feedback is cross-correlated while the learning mechanism is adjusted to maintain class distinctions. In particular, the output, e.g., the dynamic characterizing output, need not be in a steady state. In general, the output is cyclic with relatively short periods, e.g., in a range of approximately 5 cycles per second (cps) to approximately 10 cps. These cycles can be ascribed a set of semantics; sub-cycles, if any, define an instance of the defining the set of semantics, e.g., "move a finger on the right wrist." Their super-cycles, if any, define a generalization of the defining set of semantics, e.g., "move the right arm, of which the right wrist is a part."

Referring ahead to FIGS. 2-9, the neural network system and methods improve deep-learning and are operable by a set of executable instructions comprising a scalable and extensible algorithm, in accordance with embodiments of the present disclosure.

Figure 2:
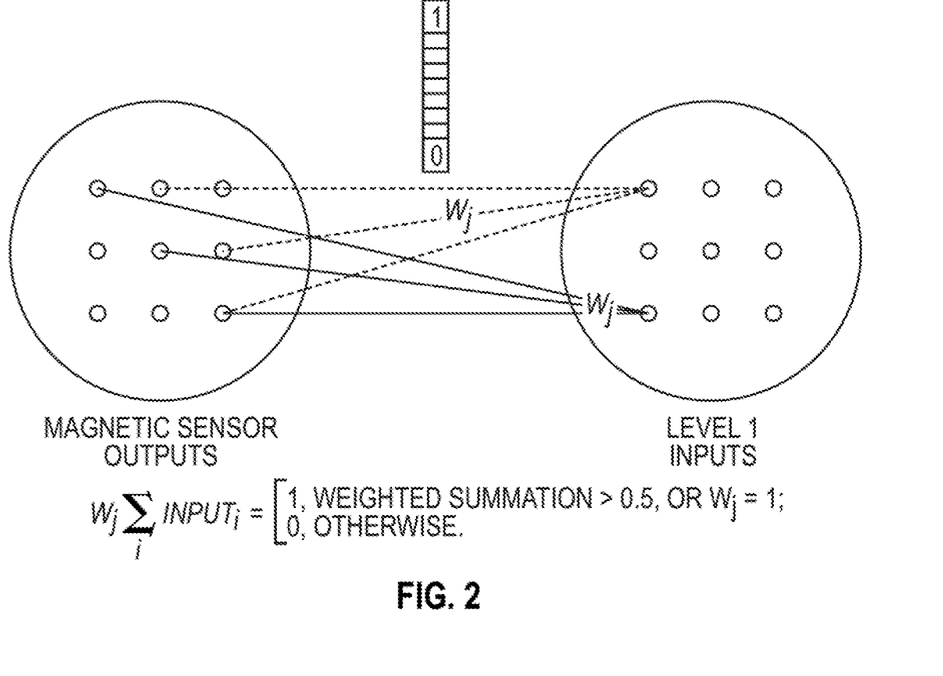
FIG. 2 is a diagram illustrating a step of mapping sensor output of the method, as shown in FIG. 9, by way of the neural network system, as shown in FIGS. 7A-7D, in accordance with an embodiment of the present disclosure.
Figure 9:
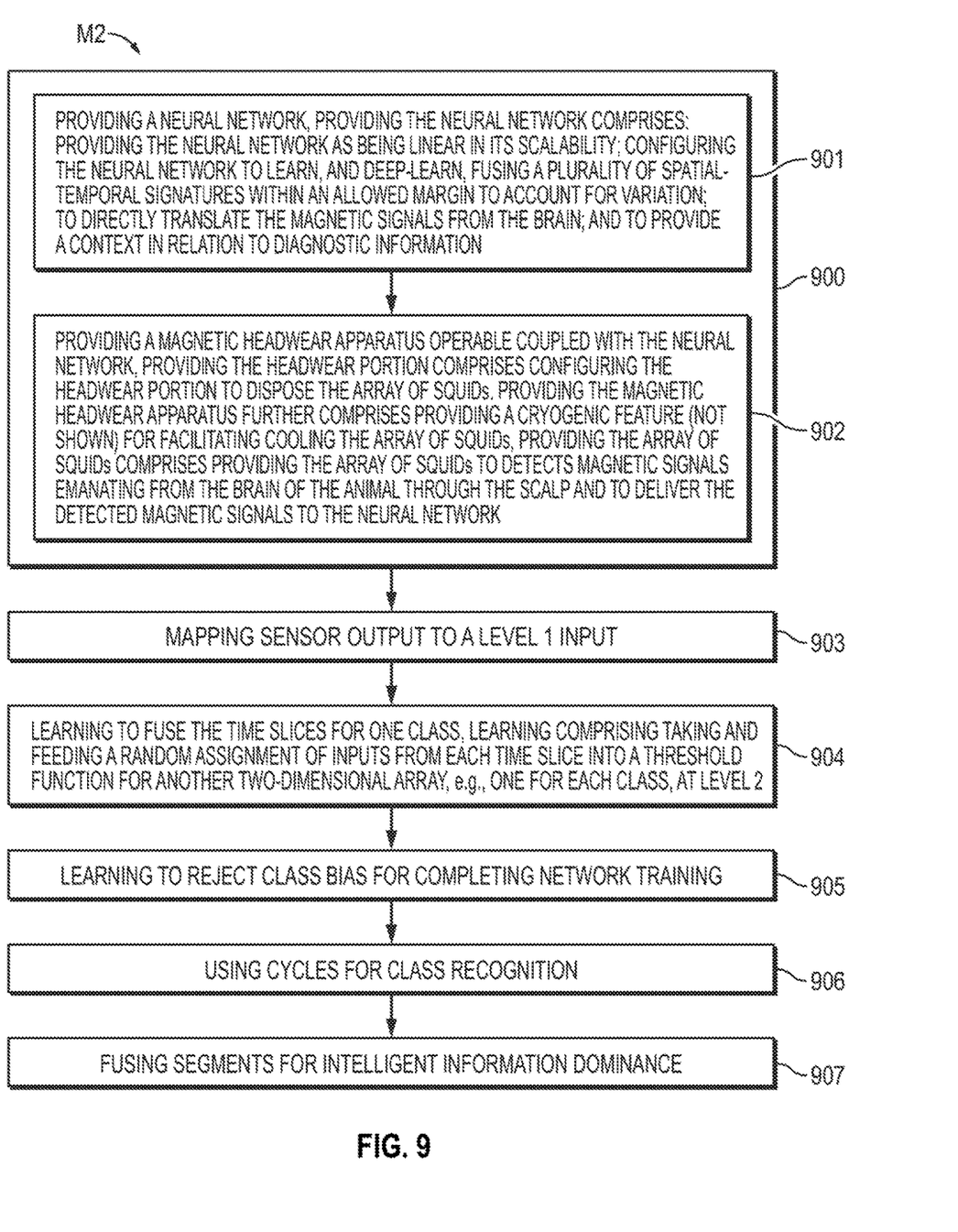
FIG. 9 is a flow diagram illustrating a method of enhancing learning by way of a neural network system, in accordance with an embodiment of the present disclosure.

Referring to FIG. 2, this diagram illustrates a step of mapping sensor output, such as magnetic sensor outputs, to a Level 1 input of the method M2, as shown in FIG. 9, by way of the neural network system S, as shown in FIGS. 7A-7D, in accordance with an embodiment of the present disclosure. Mapping comprises: obtaining and separately storing m+1 two-dimensional arrays of binary magnetic field input data at times, t, t+1, ..., t+m, which correspond to class i, where m≥1; creating a threshold function, comprising a spatial summation function and a weight (or candidate weight), e.g., one threshold function for each entry in the target array, wherein $$w_j \sum_i input_i = \{1, \text{ if the weighted summation} \geq 0.5; \text{ else } 0.\}$$

If $w_j=1$, then the output is set to 1, thereby assuring that a desired value is always mapped, wherein the candidate weights are selected from a uniform discrete interval, [0, 1], and wherein the granularity of the interval determines the number of fundamental memories which can be held and separated. If the interval is too finely set, e.g., too many subdivisions, then the problem will become intractable. However, if the interval is too coarsely set, e.g., too few subdivisions, then the problem will become unsolvable. The interval may be initialized with the cardinality equal to the number of entries in the target array.

Figure 3:
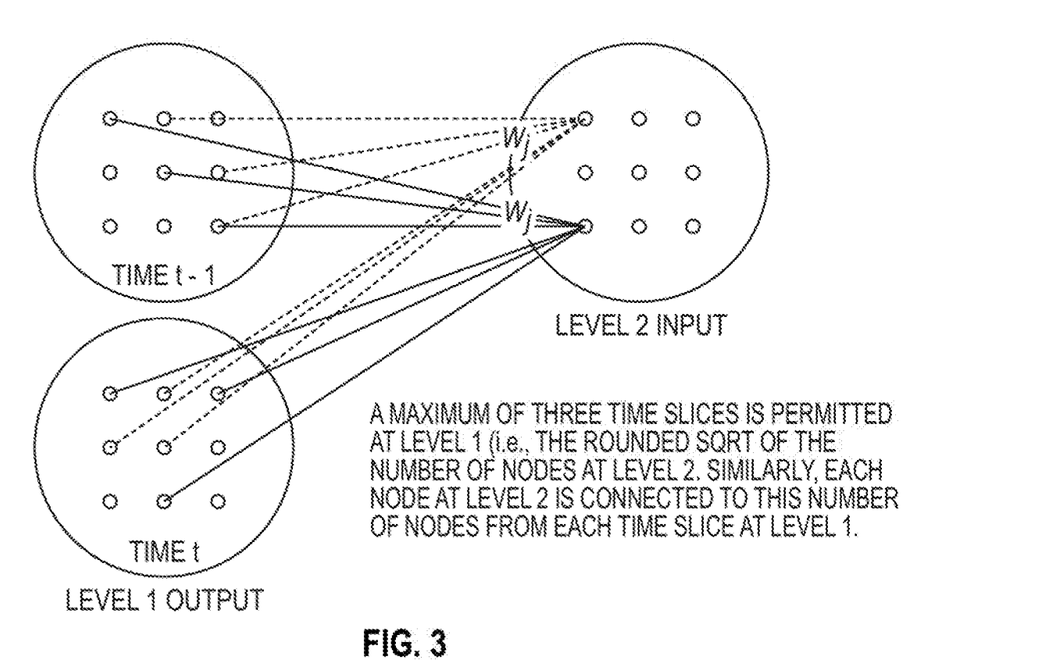
FIG. 3 is a diagram illustrating a step of learning to fuse the time slices for one class of the method, as shown in FIG. 9, by way of the neural network system, as shown in FIGS. 7A-7D, in accordance with an embodiment of the present disclosure.

Referring to FIG. 3, this diagram illustrates a step of learning to fuse a plurality of time slices for one class, learning comprising taking and feeding a random assignment of inputs from each time slice of the plurality of time slices into a threshold function for another two-dimensional array, e.g., one for each class, at Level 2 of the method M2, as shown in FIG. 9, by way of the neural network system S, as shown in FIGS. 7A-7D, in accordance with an embodiment of the present disclosure. Each time slice of the plurality of time slices comprises at least one of: (a) a time quantum or a time interval during which a time-sharing system is processing one particular computer program, (b) a time quantum or a time period for which a process is allowed to run uninterrupted in a pre-emptive multitasking operating system, and (c) a short time interval allotted to each user or each program in a multitasking or timesharing system, e.g., a short time interval on the order of milliseconds. Again, threshold functions are associated with each entry in the new array. The relationships are such that, the smaller this new array, the less resolution exists among classes, and the larger this new array, the less capability exists to generalize the classes. Thus, the array at Level 1 is taken to have the same number of nodes as the number of magnetic sensor outputs. The array at Level 2 is taken to have the same number of nodes as the number of nodes at Level 1. The inputs, from each time slice, are assigned at random. Each node at Level 2 is connected to the rounded square root of its number of nodes at each time slice at Level 1. A maximum of three time slices is permitted at Level 1, e.g., the rounded square root of the number of nodes at Level 2. Thus, at Level 1, the number of time slices cannot be greater than the rounded square root of the number of nodes at Level 2. Similarly, each node at Level 2 is connected to this number of nodes, e.g., the rounded square root of the number of nodes at Level 2, from each time slice at Level 1. If too few inputs exist, the class characterization will not be captured; however, if too many inputs exist, the class characterization will not be sufficiently generalized.

Still referring to FIG. 3, the step of learning to fuse the time slices further comprises assigning the inputs and the weights, associated with each bit in the new array, at random, such that the output of the new array is mapped, e.g., to the last time slice as a starting point. The weights are not assigned using a bisection algorithm for at least the reason that noise is needed if the weights are not to be over-optimized, where chance provides this requisite level of noise. This associates each time slice with a state meant to differentiate it from the other classes. If the last time slice is not unique, e.g., the last time slice is already associated with another class, then learning further comprises choosing another time slice and repeating the choosing step. If all such time slices are already allocated, then the learning step further comprises deleting one other intersecting class training at random, acquiring the time slice corresponding to the one other intersecting class, and retraining that class, thereby forcing that class to use a different time slice. If, after a time, this process is not converging, e.g., due to the insufficient presence of distinct time slices, the learning step further comprises setting the target as the union of the last two time slices, the last three time slices, and so on until success. If success is not achieved in this manner, the step of learning further comprises re-labeling the classes as non-separable at this chosen weight mesh.

Still referring to FIG. 3, the step of learning to fuse the time slices further comprises repeating the first step, thereby retaining a set of weights and pattern of interconnects for each class j, j≠i. Unlike the case for other hidden-layer neural networks, learning can be incrementally performed in the embodiments of the present disclosure and rarely will involve retraining the network twice for previously acquired classes, as noted above. Indeed, the larger the scale, the less the need for retraining, e.g., since the likelihood that a time slice has already been allocated progressively decreases, thereby supporting tractability. Thus, not only can the neural network system of the present disclosure run much faster than the related art conventional backprop, say, but the neural network system of the present disclosure is amenable to parallel processing and energy conservation. The latter follows for at least that the neural network system can be idled for existing classes when training to acquire a new class (unlike backprop, which must be rerun multiple times for all classes every time a new class is to be acquired).

Figure 4:
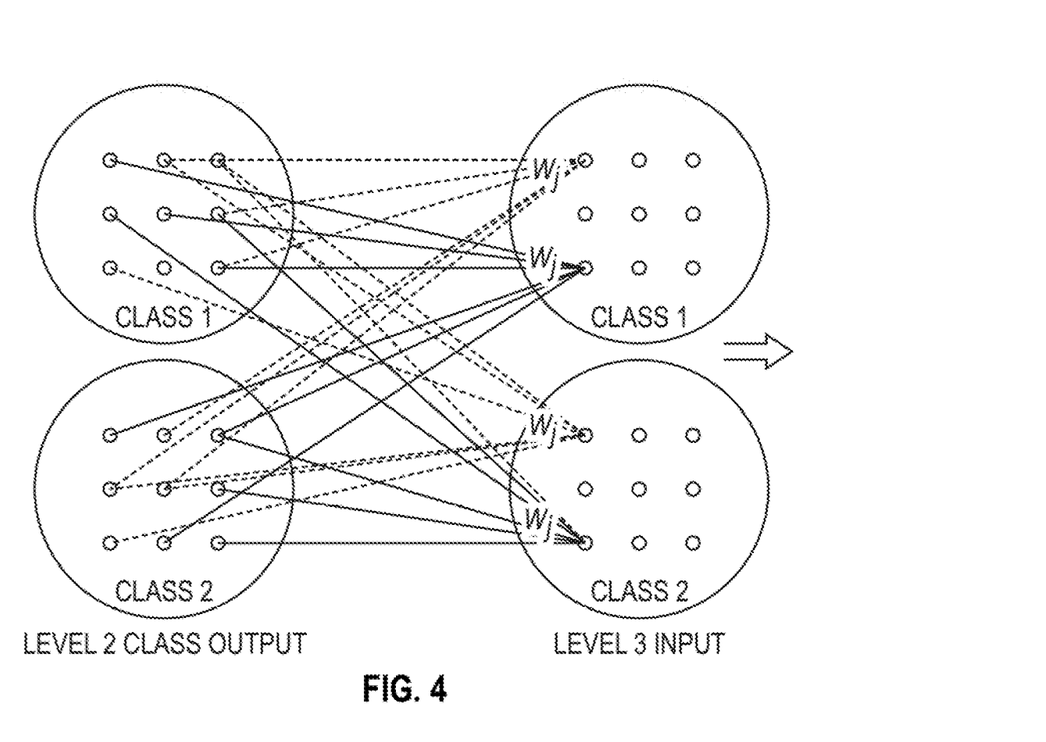
FIG. 4 is a diagram illustrating a step of learning to reject class bias for completing network training of the method, as shown in FIG. 9, by way of the neural network system, as shown in FIGS. 7A-7D, in accordance with an embodiment of the present disclosure.

Referring to FIG. 4, this diagram illustrates a step of learning to reject class bias for completing network training of the method M2, as shown in FIG. 9, by way of the neural network system S, as shown in FIGS. 7A-7D, in accordance with an embodiment of the present disclosure. To complete the network training, the system S must learn to reject the bias introduced by distinct classes and their generalizations. Thus, the outputs, for each class, are randomly connected to yet another new array (layer) at Level 3. Each node at Level 3 is connected to the rounded square root of its number of nodes for each class at Level 2. A maximum of three time slices is permitted at Level 2, e.g., the rounded square root of the number of nodes at Level 3. Thus, at Level 2, the number of time slices cannot be greater than the rounded square root of the number of nodes at Level 3. Similarly, each node at Level 3 is connected to this number of nodes, e.g., the rounded square root of the number of nodes at Level 3, from each time slice at Level 2. If too few inputs exist, the next level will be susceptible to class identification errors; however, if too many inputs exist, the class identification errors will not be sufficiently generalized. FIG. 4 also shows that noise may approximate class firings at Level 2. However, this noise is filtered at Level 3, which minimizes any chosen error norm, e.g., the 2-norm, the infinite norm, and so forth, thereby properly activating only the correct class which will be the one class having a minimal error.

Still referring to FIG. 4, the step of learning to reject class bias further comprises assigning the inputs and the weights, associated with each entry at Level 2, at random, wherein the output of the new array at Level 3 is the originating class pattern at Level 2, when the other classes at Level 2 provide random noise output, which is skewed by being out of the originating class pattern, thereby annealing recognition through the use of the 2-norm or the infinite norm at Level 3. This step of assigning the inputs and the weights is performed for each class. If success is not achieved in this manner, the step of learning to reject class bias further comprises re-labeling the classes as non-separable at this chosen weight mesh. The requisite storage is O(number of classes×number of entries per class). The runtime, which is $O(cln^2)$, where c is a constant of proportionality, which adjusts for the complexity of finding the weights, l is the number of levels, and n is the number of nodes in an array at each level, only grows linearly with the number of classes; and, hence, can always be rendered tractable for a given number of nodes per level, unlike conventional neural networks. This step of re-labeling can be accomplished by having a sufficient number of parallel processors, in contrast to conventional hidden-layer neural networks. Noteworthy is that any other neural network, having a hidden layer, is NP-hard, which is a far worse circumstance as such conventional neural networks are unscalable.

Figure 5:
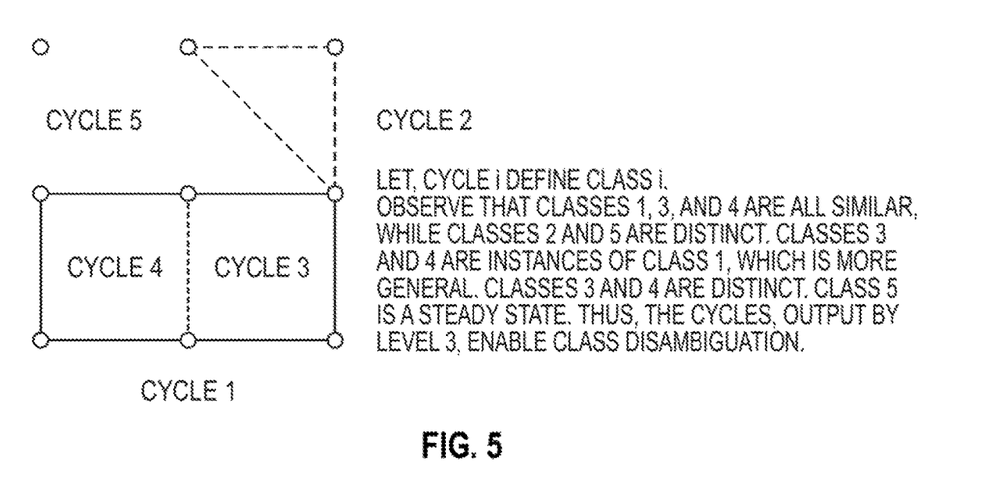
FIG. 5 is a diagram illustrating a step of using cycles for class recognition of the method, as shown in FIG. 9, by way of the neural network system, as shown in FIGS. 7A-7D, in accordance with an embodiment of the present disclosure.

Referring to FIG. 5, this diagram illustrates a step of using cycles for class recognition of the method M2, as shown in FIG. 9, by way of the neural network system S, as shown in FIGS. 7A-7D, in accordance with an embodiment of the present disclosure. The use of feedback, as shown in FIG. 4, may cause oscillations in the final output array. Each cycle corresponds to a distinct class; and, in the method M2, that final disambiguation is made. Using cycles for class recognition comprises defining a fundamental cycle, in graph theory, to be a sequence of states, which recurs and from which all other cycles can be extracted. Each class will induce a steady state, e.g., a fundamental cycle of a single node, or a cycle comprised of more than one node. By defining the cycle, produced by each class, to be fundamental, super cycles are mappable to their nearest class, comprising a composition of fundamental cycles, whereby identification of previously unseen characterizations in terms of their class mappings is achievable, and whereby a list of classes to which the identification is similar, if any, is provided. Further training will remove any ambiguity.

Figure 6:
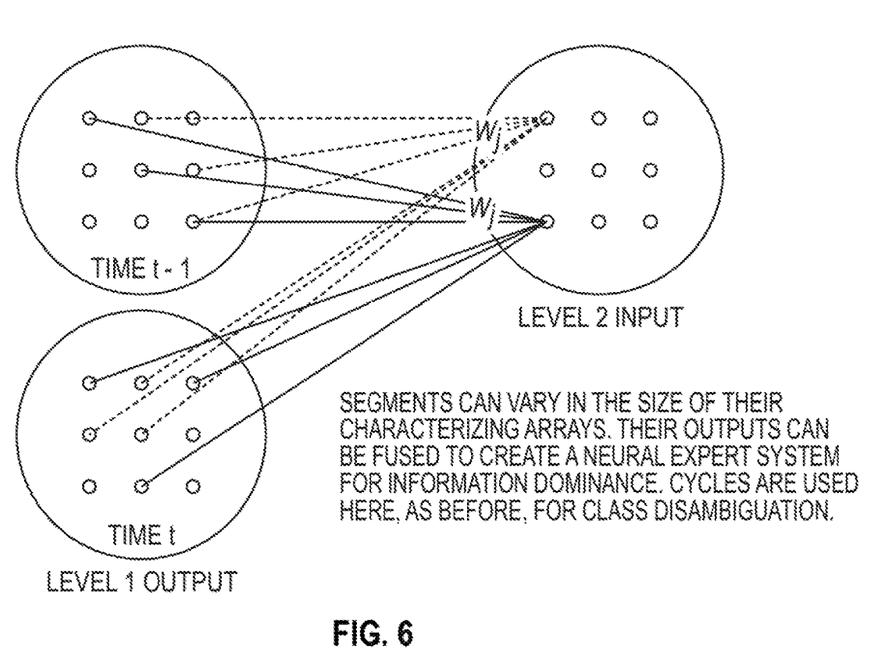
FIG. 6 is a diagram illustrating a step of fusing segments for intelligent information dominance of the method, as shown in FIG. 9, by way of the neural network system, as shown in FIGS. 7A-7D, in accordance with an embodiment of the present disclosure.

Referring to FIG. 6, this diagram illustrates a step of fusing segments for intelligent information dominance of the method M2, as shown in FIG. 9, by way of the neural network system S, as shown in FIGS. 7A-7D, in accordance with an embodiment of the present disclosure. If the aforementioned steps define a segment, then fusing, by cross-coupling segments, can provide for tractable learning of even greater complexity. Segments can vary in the size of their characterizing arrays as well as in their associated weight granularities. Fusing segments is useful for hierarchical classification and recognition. Fusing segments can be used to create a neural expert system capable of modus ponens (in contrast to conventional neural networks) and fusing many domains for intelligent decision-making, thereby providing information dominance.

Figure 7A:
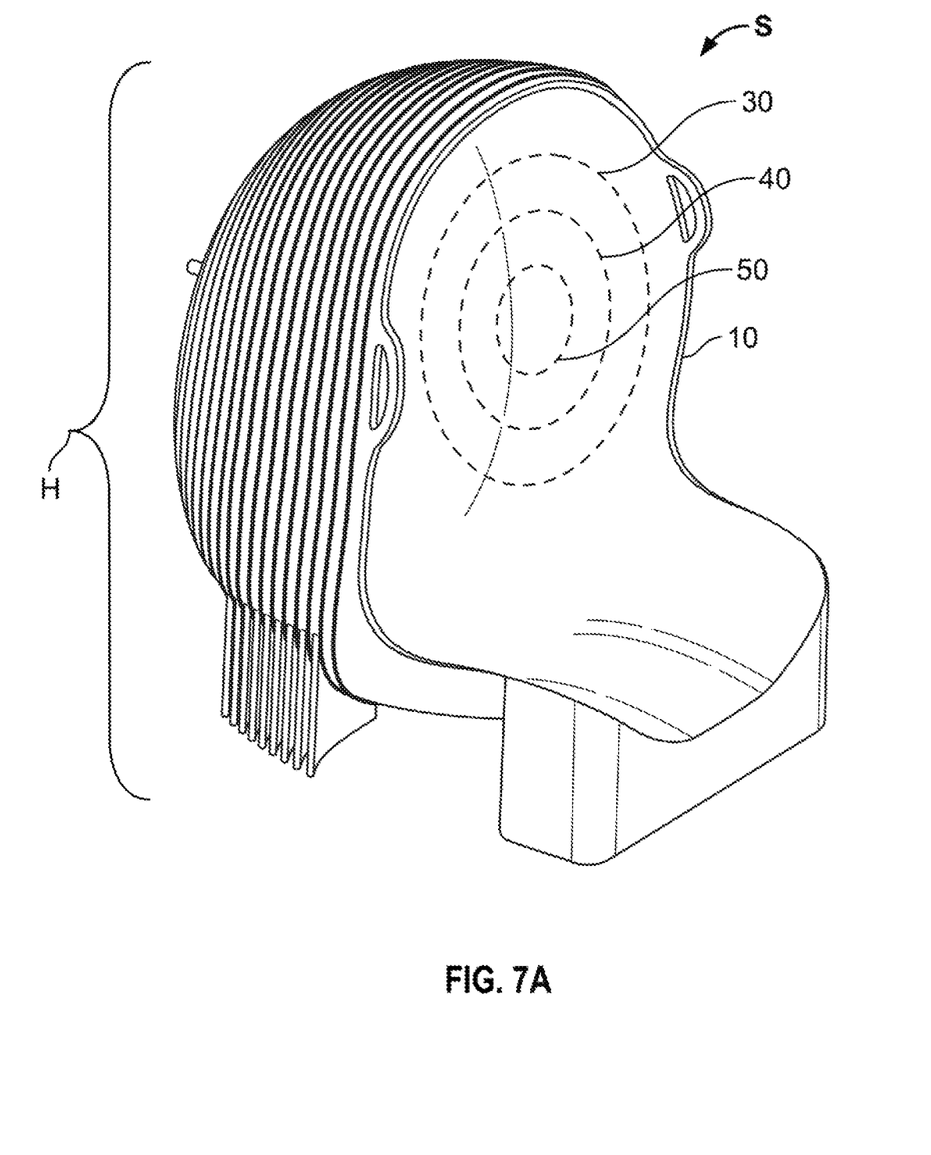
FIG. 7A is a diagram illustrating, in a perspective view, a neural network system, in accordance with an embodiment of the present disclosure.

Referring to FIG. 7A, this diagram illustrates a perspective view of a neural network system S, in accordance with an embodiment of the present disclosure. The system S comprises: a neural network N (FIG. 7D), the neural network N configured to: map sensor output to a Level 1 input; learn to fuse the time slices for one class, learning comprising taking and feeding a random assignment of inputs from each time slice into a threshold function for another two-dimensional array; learn to reject class bias for completing network training; use cycles for class recognition; and fuse segments for intelligent information dominance; and a magnetic headwear apparatus H operable coupled with the neural network N. The neural network N is linear in its scalability; and the neural network N is configured to learn, and deep-learn, fusing a plurality of spatial-temporal signatures within an allowed margin to account for variation. The neural network N is configured to detect and interpret the magnetic signals from the brain 50. The neural network N is further configured to directly translate the magnetic signals from the brain 50 and to provide a context in relation to diagnostic information.

Figure 7B:
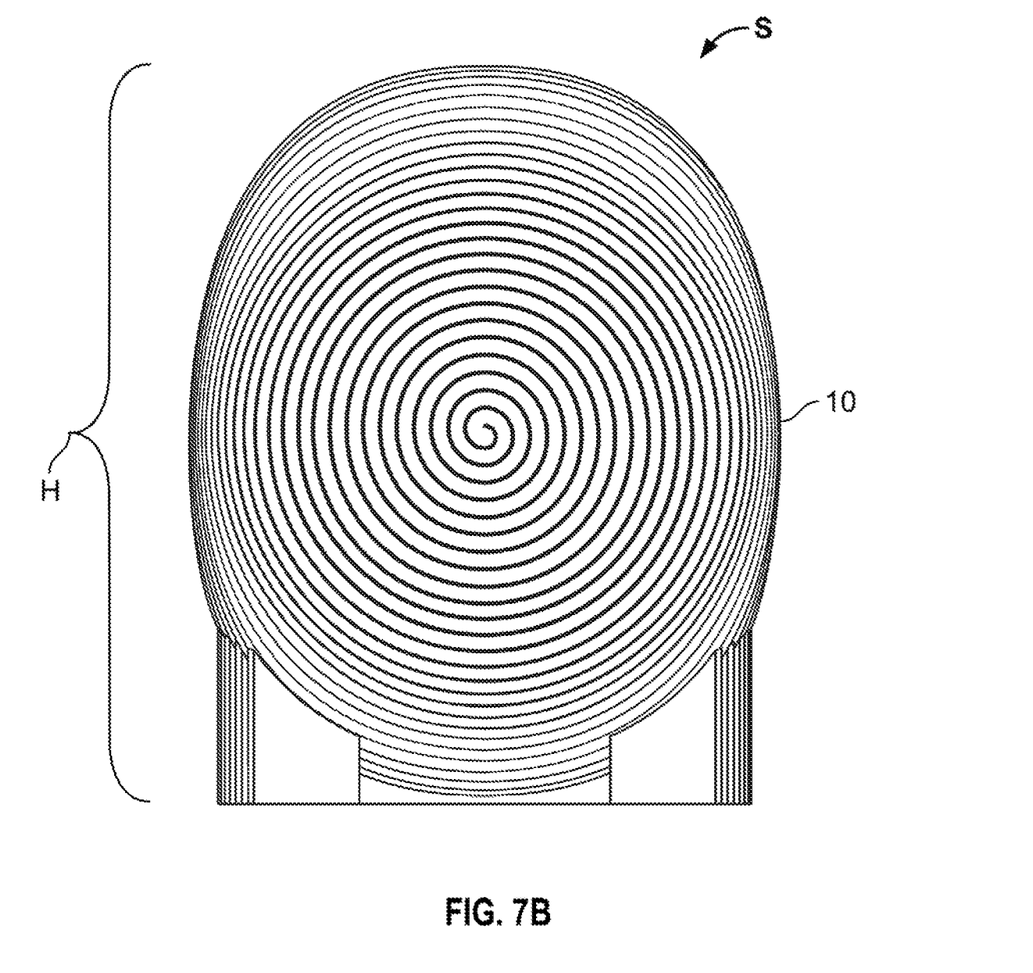
FIG. 7B is a diagram illustrating, in a rear view, a neural network system, as shown in FIG. 7A, in accordance with an embodiment of the present disclosure.

Referring to FIG. 7B, this diagram illustrates a rear view of a neural network system S, as shown in FIG. 7A, in accordance with an embodiment of the present disclosure. The magnetic headwear apparatus H comprises: a headwear portion 10, the headwear portion 10 comprising a helmet configuration, e.g., a football helmet configuration; and an array of SQUIDs 20 disposed in relation to the headwear portion 10. The headwear portion 10 is configured to dispose the array of SQUIDs 20 in close proximity to a scalp 30, e.g., in a range of approximately 0.1 inch to approximately 0.13 inch, of an animal, such as a human being.

Figure 7C:
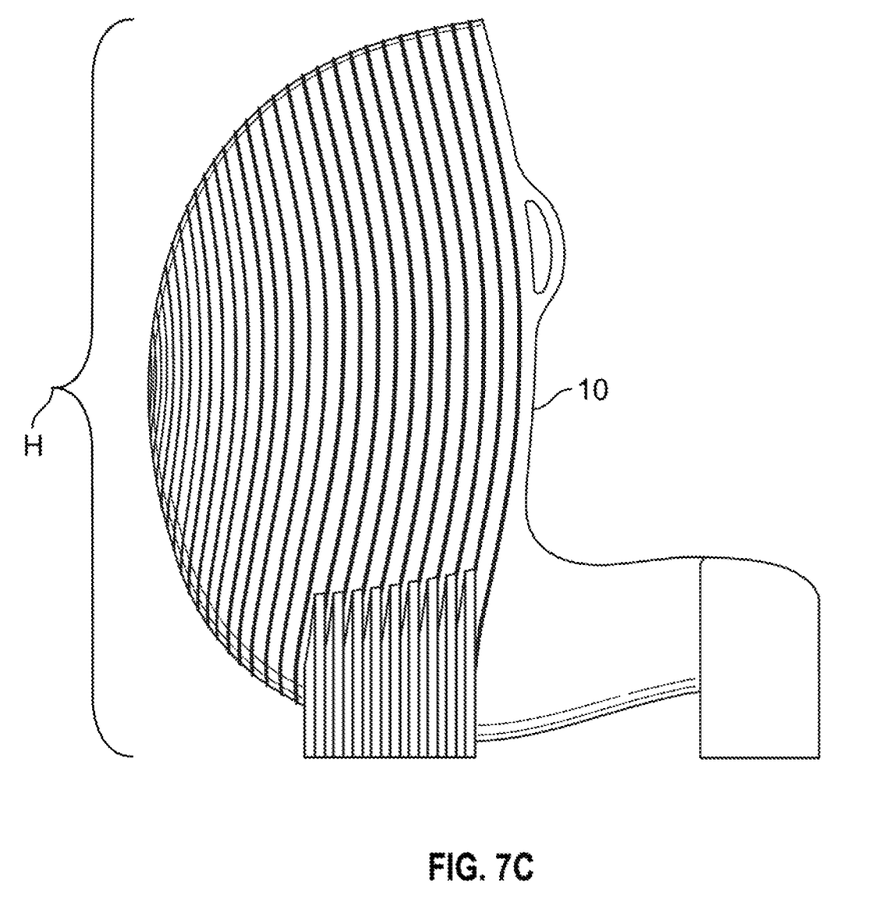
FIG. 7C is diagram illustrating, in a side view, a neural network system, as shown in FIGS. 7A and 7B, in accordance with an embodiment of the present disclosure.

Referring to FIG. 7C, this diagram illustrates a side view of a neural network system S, as shown in FIGS. 7A and 7B, in accordance with an embodiment of the present disclosure. The magnetic headwear apparatus H further comprises a cooling feature, e.g., a cryogenic feature (FIG. 7D) for facilitating cooling the array of SQUIDs 20. The array of SQUIDs 20 detects magnetic signals emanating from the brain 50 of the animal through the skull 40 and the scalp 30 and delivers the detected magnetic signals to the neural network N.

Figure 7D:
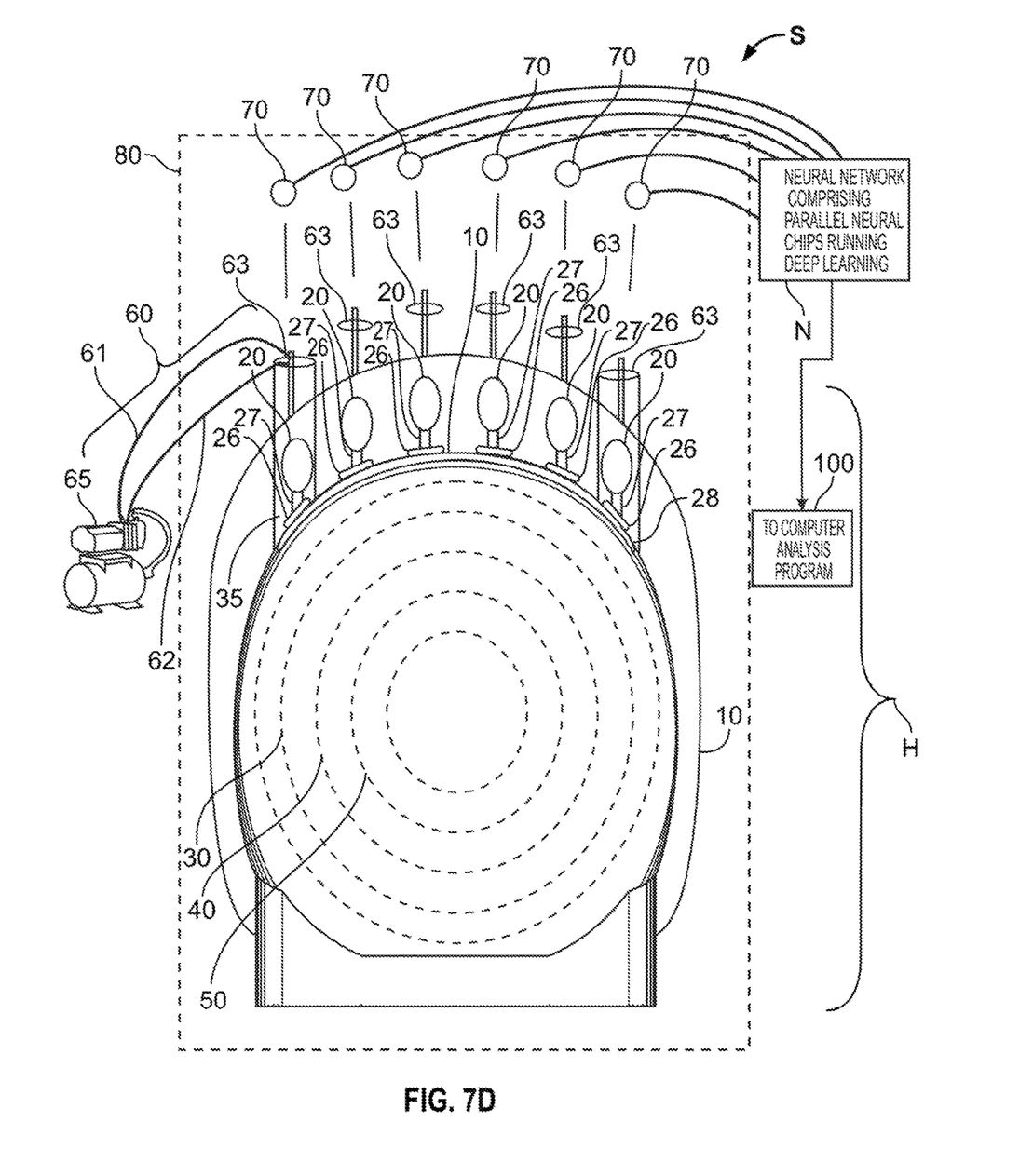
FIG. 7D is a diagram illustrating, in a rear view, the neural network system, as shown in FIGS. 7A-7C, in accordance with an embodiment of the present disclosure.

Referring to FIG. 7D, this diagram illustrates an interior view of the neural network system S, comprising the magnetic headwear apparatus H, e.g., a head coil apparatus, as shown in FIGS. 7A-7C), in accordance with an embodiment of the present disclosure. For example, the magnetic headwear apparatus H comprises a headwear portion 10 having a padded portion 11, wherein the padded portion 11 provides both mechanical protection in cushioning the scalp 30, the skull 40, and the brain 50, and wherein the padded portion 11 further provides thermal insulation for the array of SQUIDs 20, e.g., by preventing heat absorption otherwise transferrable from external factors as well as from an environment of the scalp 30 or the skull 40 themselves. The cryogenic feature comprises at least one of a tubular structure 60, having delivery tubing 61 and return tubing 62, and a channel structure 63 configured to accommodate, and circulate, a cryogenic liquid, e.g., cryogenic helium (LHe), through the array of SQUIDs 20. The cryogenic liquid is providable from a portable Dewar (not shown), e.g., being pumped by way of a compressor 65, e.g., a hermetically-sealed compressor. The cryogenic feature is a closed system, whereby the coolant circulates through the tubular structure 60. The tubular structure 60 comprises a metal, such as silver (Ag), copper (Cu), and aluminum (Al). In some embodiments, the cooling or cryogenic feature comprises thermistors.

Still referring to FIG. 7D, the array of SQUIDs 20 or SQUID array transforms magnetic impulses from the skull 40 into electrical signals, wherein the electrical signals are digitized for input into the neural network N. Each SQUID 20 of the array of SQUIDs 20 allows for a variable capacitance, e.g., set by an external computer 100, operable by a set of executable instructions storable in relation to a non-transient memory device, to provide temporal summation of the magnetic signal and to provide more rejection, or less rejection, of bias noise, e.g., via corresponding capacitors 70 operable via parasitic capacitance, whereby magnetoencephalography provides improved outcomes over related art electrical encephalography. For at least consideration that magnetic energy dissipates as a fourth power of a distance from a source, the array of SQUIDs 20 are disposed in as close proximity to the skull 40 as practical, e.g., in a range of approximately 0.1 in to approximately 0.13 in. The neural network N comprises parallel neural chips for performing or running deep learning tasks. The external computer 100 is further configured, by the set of executable instructions, to tune the capacitors 70, wherein the capacitors 70 are coupled with the neural network N. The system S operates in a temperature range of approximately 77 Kelvin. The array of SQ UIDS 20 also operate by way of a parasitic capacitance on an electrical bus, whereby magnetically-induced eddy currents are smoothed.

Still referring to FIG. 7D, by example only, each SQUID 20 comprises a flat-head configuration, the flat-head configuration comprising a flat-head portion 26 and a stem portion 27, wherein the flat-head portion 26 is configured to contact the skull, and wherein the stem portion 27 points away from the skull and is disposed into the headwear portion 10. The magnetic headwear apparatus H further comprises a separator 28 disposed between the skull and the array of SQUIDs 20, the separator 28 comprising a separator material being magnetically permeable cryogenically insulative. For example, the separator material comprises a Styrofoam material, and a thickness in a range of approximately 1/16 inch (in) to approximately 1/8 in, preferably a thick ness of approximately 0.125 in. The entire array of SQUIDs 20 and associated wiring are disposable within a Faraday cage 80 to prevent at least one of radio frequency (RF) interference and electrical interference. Accordingly, the system S may not be used in the presence of external magnetic fields. Springs, such as small "pen" springs are implemented for elastically coupling at least one of the array of SQUIDS 20 to the separator 28 and the separator 28 to the scalp 30.

Figure 7E:
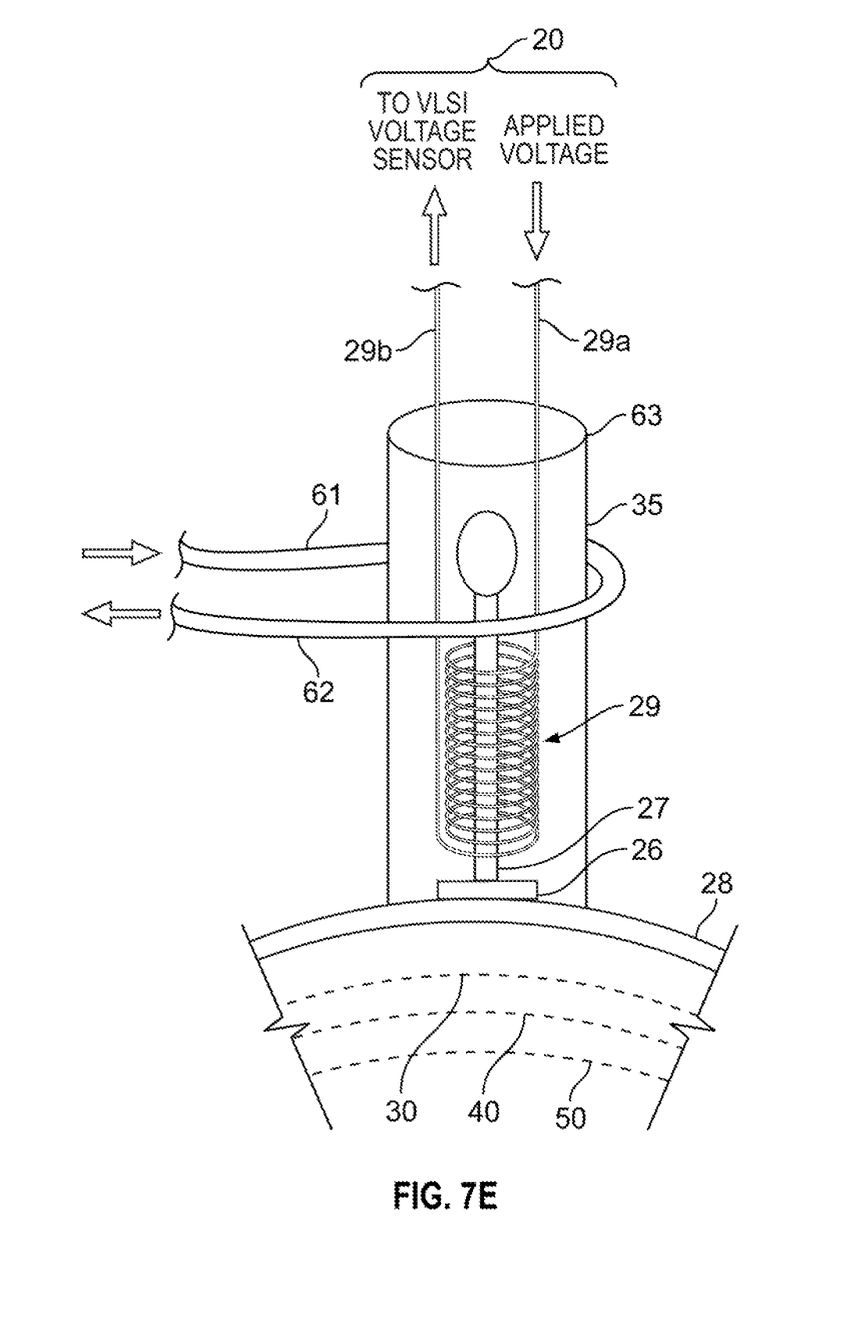
FIG. 7E is a diagram illustrating, in a side view, a magnetic sensor, implementable in a neural network system, in accordance with an embodiment of the present disclosure.

Referring to FIG. 7E, this diagram illustrates a side view of a magnetic sensor or SQUID 20 comprising, implementable in a neural network system S, in accordance with an embodiment of the present disclosure. The magnetic sensor or SQUID 20 comprises a stem portion 27 and flat-head portion 26 coupled with the stem portion 27, at least one electromagnetic winding element 29 disposed or wound around the stem portion 27. The electromagnetic winding element 29 comprises an applied voltage portion 29a electrically coupled with a voltage source and a sensed voltage portion 29b electrically coupled with a VLSI voltage sensor (not shown). In some embodiments, a nail assembly comprises the stem portion 27 disposed in a tube portion (not shown) comprising rolled aluminum foil and paper, wherein the tube portion comprises a coating, such as polyethylene, and is sealed in a high vacuum, whereby thermal insulation is provided. The tube portion comprises an inner diameter or cross-sectional dimension of approximately 0.5 inch. The tube portion comprises an end portion disposed proximate the scalp 30. The end portion comprises a protective layer, the protective layer comprising a thermally-insulating layer, such as Styrofoam, and an acoustically-insulating material.

Still referring to FIG. 7E, the electromagnetic winding element 29 comprises a thin wire, e.g., having diameter or other cross-sectional dimension in a range of approximately 10 microns to approximately 200 microns. The thin wire comprises an electrically insulating coating, such as a silicone layer. For example, the thin wire comprises at least one of a resistive wire, a magnetic material, such as a cobalt-iron alloy, a cobalt-core wire, a 2G high-temperature superconducting (HTS) wire, such as FUJIKURA® 2G HTS wire, an yttrium-gadolinium-based material, an yttrium-barium-copper oxide (YBCO) material, a material having a critical temperature of 77 Kelvin, e.g., obtained using liquid nitrogen ($LN_2$) or liquid air. The electromagnetic winding element 29 further comprises at least one resistor that is serially disposed in alternative embodiments. The VLSI voltage sensor comprises an electrical bus and is configured to sense J-K flip-flops. The applied voltage portion 29a and the sensed voltage portion 29b are threaded through a cannula 35 formed in the headwear portion 10.

Still referring to FIG. 7E, the tubular structure 60, such as a "U-tube," delivers a cryogenic fluid via the delivery tubing 21, wherein the return tubing 62 returns the cryogenic fluid to the cryogenic feature, whereby the SQUID 20 is cooled. The cryogenic feature comprises a gas expansion feature configured to deliver the cryogenic fluid at a pressure in a range of approximately 3000 psi to approximately 5000 psi. The tubular structure 60 comprises a diameter or cross-sectional dimension in a range of approximately 0.5 inch. In order to maintain purity of a coolant comprising air, the coolant is transmitted through at least one of a mechanical filter (not shown) for removing larger particles, a desiccant (not shown), such as a calcium chloride ($CaCl_2$) filter, for removing water molecules, wherein the $CaCl_2$ filter is recyclable via heating, a carbon dioxide filter, such as sodium hydroxide (NaOH), for removing carbon dioxide ($CO_2$), and a silica ($SiO2$) gel filter or a charcoal filter for removing toxins, whereby clogging of the tubular structure 60 is prevented. The cooling or cryogenic feature comprises a compressor 65, such as a scuba tank compressor or an aqualung tank compressor having a heat exchanger and a pressure regulator.

Still referring to FIG. 7E, the separator 28 spaces the flat-head portion 26 from the scalp 30 and comprises a thickness in a range of approximately 1/16 inch to approximately 1/8 inch. The separator 28 comprises any material which is thermally-insulating as well as magnetically-permeable, such as at least one of Styrofoam, polyethylene, polypropylene, nylon, and the like.

Figure 8:
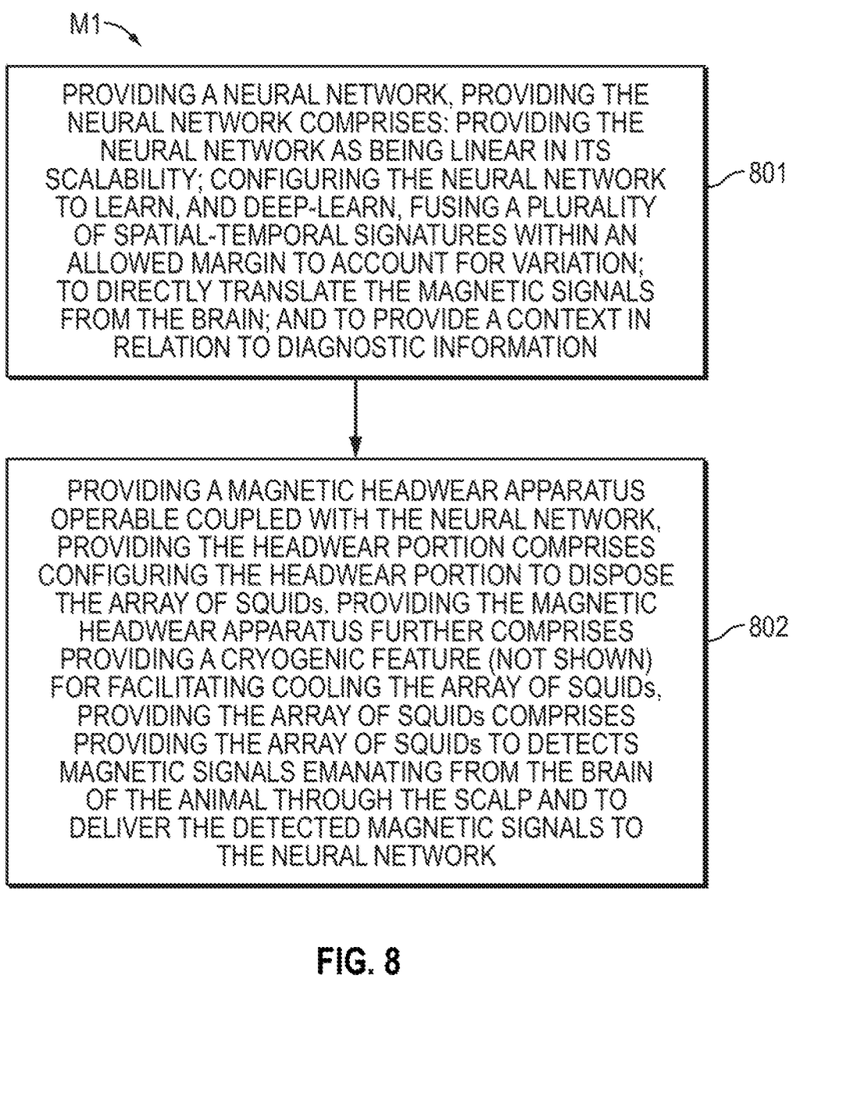
FIG. 8 is a flow diagram illustrating a method of fabricating a neural network system for enhancing deep-learning, in accordance with an embodiment of the present disclosure.

Referring to FIG. 8, this flow diagram illustrates a method M1 of fabricating a neural network system S, in accordance with an embodiment of the present disclosure. The method M1 comprises: providing a neural network N, as indicated by block 801; and providing a magnetic headwear apparatus H operably coupled with the neural network N, as indicated by block 802. Providing the magnetic headwear apparatus H, as indicated by block 802, comprises: providing a headwear portion 10; and providing an array of SQUIDs 20 disposed in relation to the headwear portion 10. Providing the headwear portion 10 comprises configuring the headwear portion 10 to dispose the array of SQUIDs 20 in close proximity to a scalp 30, e.g., in a range of approximately 0.1 in to approximately 0.13 in, of an animal, such as a human being. Providing the magnetic headwear apparatus H further comprises providing a cryogenic feature (not shown) for facilitating cooling the array of SQUIDs 20. Providing the array of SQUIDs 20 comprises providing the array of SQUIDs 20 to detect magnetic signals emanating from the brain 50 of the animal through the scalp 30 and to deliver the detected magnetic signals to the neural network N. Providing the neural network N comprises: providing the neural network N as being linear in its scalability; configuring the neural network N to learn, and deep-learn, fusing a plurality of spatial-temporal signatures within an allowed margin to account for variation; to directly translate the magnetic signals from the brain 50; and to provide a context in relation to diagnostic information.

Referring to FIG. 9, this flow diagram illustrates a method M2 of enhancing learning by way of a neural network system S, in accordance with an embodiment of the present disclosure. The method M2 comprises: providing the neural network system S, as indicated by block 900, providing the neural network system S comprising: providing a neural network N, as indicated by block 901; and providing a magnetic headwear apparatus H operably coupled with the neural network N, as indicated by block 902; mapping sensor output to a Level 1 input, as indicated by block 903; learning to fuse the time slices for one class, learning comprising taking and feeding a random assignment of inputs from each time slice into a threshold function for another two-dimensional array, e.g., one for each class, at Level 2, as indicated by block 904; learning to reject class bias for completing network training, as indicated by block 905; using cycles for class recognition, as indicated by block 906; and fusing segments for intelligent information dominance, as indicated by block 907. Substeps of the method M2 have been described in relation to FIGS. 2-5.

Referring back to FIGS. 2-9, the neural network system and methods of the present disclosure encompass features, implantations, and/or alternative embodiments that include, but are not limited to, (a) tractable scalable learning using only linear increases in spatial requirements, (b) mapping groups, (c) fusing problems which are too large for conventional neural networks to handle, (d) assignable group membership using fundamental cycles in the net states, (e) mind-control of military systems, prosthetic limb control, and portable brain imaging, (f) mapping active or passive sonar signals to a source characterization, e.g., by fusing a plethora of space-time waveforms, each having different frequencies and times of arrival, tractable learning speeds, and large memory stores, wherein characterizations are not amenable to symbolic processing until the final stage, wherein the composite signal is mapped onto a stock image, e.g., a particular class of submarine, (g) laser and/or maser imaging of targets by fusing hyperspectral reflections, (h) autonomous guidance, e.g., unmanned vehicles, (i) operable across massively parallel/distributed processors, (j) energy conservative by powering only the active groups during training, e.g., polynomial time training saving exponential energy over NP-hard neural networks, (k) ensuring that every neuron learns a proper map by setting the weight to unity for foreign firing of the neuron, regardless of an insufficient space-time summation, (l) inhibitory neurons resulting from multiplication by zero weights, (m) preventing a combinatoric explosion by having the same number of neurons at each level, and (n) image recognition for fusing a large number of images and/or video with sound, thereby providing a recognition system that is more useful than related art recognition systems.

In addition, the following documents are hereby incorporated by reference in their entirety: Rubin, Stuart H. "Kaser: Knowledge Amplification by Structured Expert Randomization: IEEE Transactions on Systems, Man, and Cybernetics—Part B: Cybernetics, Vol. 34, No. 6 (December 2004); Rubin, S. H., "On randomization and discovery," Information Sciences, Vol. 177, Issue 1, pp. 170-191 (Jan. 1, 2007); and Rubin, Stuart H., "Geodesic Miner: Natural Language Communications between Humans and Information Systems," Aug. 16, 2006; and any features disclosed therein are combinable with any features in the present disclosure. Any such combination of features is encompassed by the present disclosure.

Understood is that many additional changes in the details, materials, steps and arrangement of parts, which have been herein described and illustrated to explain the nature of the invention, may be made by those skilled in the art within the principle and scope of the invention as expressed in the appended claims.

What is claimed:
1. A neural network system, comprising:
a neural network, comprising a two-dimensional array of nodes, where each node represents an artificial neuron in the neural network, configured to achieve intelligent information dominance through tractable deep learning, comprising:
a processor and non-transient memory device storing a set of executable instructions configured to:
map sensor output at a first level wherein at the first level there is a sensor output for each node of the neural network;
randomly sampling consecutive sensor outputs of the plurality of time slices to:
fuse a plurality of time slices to determine a class,
reject class bias in completing training;
detect the number of cycles to determine class recognition; and
fuse segments characterizing the two-dimensional arrays as well as in their associated weight granularities for use in hierarchical classification and recognition, and
a magnetic headwear apparatus operably coupled with the neural network.
2. The system of claim 1, wherein the magnetic headwear apparatus comprises:
a headwear portion; and
an array of superconducting quantum interfere devices ("SQUIDs") disposed in relation to the headwear portion, wherein the array of SQUIDS are configured to detect a magnetic signal in a range of $10^{-9}$ teslas to $10^{-6}$ teslas.
3. The system of claim 2, wherein the headwear portion is configured to dispose the array of SQUIDs in close proximity to a scalp in a range of 0.1 in to 0.13 in.
4. The system of claim 2, wherein the magnetic headwear apparatus further comprises a cryogenic feature for facilitating cooling the array of SQUIDs.
5. The system of claim 3, wherein the array of SQUIDs is configured to:
detect magnetic signals emanating from a brain through the scalp, and
deliver the detected magnetic signals to the neural network.
6. The system of claim 1, wherein the neural network is linear in its scalability.

7. The system of claim 1, wherein the neural network is configured to at least one of learn and deep-learn fusing a plurality of spatial-temporal signatures.

8. The system of claim 5, wherein the neural network is configured to detect and interpret the magnetic signals from the brain.

9. The system of claim 5, wherein the neural network is configured to directly translate the magnetic signals from the brain.

10. The system of claim 1, wherein the neural network is configured to provide a context in relation to diagnostic information.

11. A method of fabricating a neural network system, comprising:
providing a tractable neural network, the tractable neural network configured to:
map sensor output at a first level wherein at the first level there is a sensor output for each node of the neural network;
randomly sampling consecutive sensor outputs of the plurality of time slices to:
fuse a plurality of time slices to determine a class,
reject class bias in completing training;
detect the number of cycles to determine class recognition; and
fuse segments characterizing the two-dimensional arrays as well as in their associated weight granularities for use in hierarchical classification and recognition; and
providing a magnetic headwear apparatus operably coupled with the neural network.

12. The method of claim 11, wherein the magnetic headwear apparatus comprises:
a headwear portion; and
an array of superconducting quantum interfere devices ("SQUIDs") disposed in relation to the headwear portion.

13. The method of claim 12, wherein the headwear portion is configured to dispose the array of SQUIDs in close proximity to a scalp in a range of approximately 0.1 in to approximately 0.13 in.

14. The method of claim 12, wherein the magnetic headwear apparatus further comprises a cryogenic feature for facilitating cooling the array of SQUIDs.

15. The method of claim 13, wherein the array of SQUIDs is configured to:
detect magnetic signals emanating from a brain through the scalp, and
deliver the detected magnetic signals to the neural network.

16. The method of claim 11, wherein the neural network is linear in its scalability.

17. The method of claim 11, wherein the neural network is configured to at least one of learn and deep-learn fusing a plurality of spatial-temporal signatures.

18. The method of claim 15, wherein the neural network is configured to detect and interpret the magnetic signals from the brain.

19. The method of claim 15,
wherein the neural network is configured to directly translate the magnetic signals from the brain, and
wherein the neural network is configured to provide a context in relation to diagnostic information.

20. A method of improving deep learning by way of a tractable neural network system, comprising:
providing the tractable neural network system, comprising:
providing a neural network, the neural network configured to:
map sensor output at a first level wherein at the first level there is a sensor output for each node of the neural network;
randomly sampling consecutive sensor outputs of the plurality of time slices to:
fuse a plurality of time slices to determine a class,
reject class bias in completing training;
detect the number of cycles to determine class recognition; and
fuse segments characterizing the two-dimensional arrays as well as in their associated weight granularities for use in hierarchical classification and recognition; and
providing a magnetic headwear apparatus operably coupled with the neural network;
map sensor output at a first level wherein at the first level there is a sensor output for each node of the neural network;
randomly sampling consecutive sensor outputs of the plurality of time slices to:
fuse a plurality of time slices to determine a class,
reject class bias in completing training;
detect the number of cycles to determine class recognition; and
fuse segments characterizing the two-dimensional arrays as well as in their associated weight granularities for use in hierarchical classification and recognition.

\* \* \* \* \*